US006439276B1

United States Patent
Wood et al.

(10) Patent No.: US 6,439,276 B1
(45) Date of Patent: Aug. 27, 2002

(54) KIT FOR LOADING AND DISPOSAL OF HYPODERMIC SYRINGES USED FOR ADMINISTERING MEDICATION

(75) Inventors: Clifford Wood, Pound Ridge, NY (US); Ted Stiles, Tewksbury, NJ (US); David Bragin, Brooklyn, NY (US)

(73) Assignee: Trimensions, Inc., New York, NY (US)

( * ) Notice: Subject to any disclaimer, the term of this patent is extended or adjusted under 35 U.S.C. 154(b) by 0 days.

(21) Appl. No.: 09/900,366

(22) Filed: Jul. 6, 2001

(51) Int. Cl.[7] .............................. B65B 1/04; B65B 3/04; B67C 3/02
(52) U.S. Cl. ............................ 141/97; 141/27; 141/94; 141/375; 141/383; 604/414; 206/365
(58) Field of Search ................................. 141/25–27, 94, 141/97, 329, 375, 383; 604/403, 411, 413, 414, 187, 207, 208; 206/365, 366

(56) References Cited

U.S. PATENT DOCUMENTS 4,121,755 A * 10/1978 Meseke et al. ............. 206/366
4,969,554 A * 11/1990 Sawaya ...................... 206/210
6,364,866 B1 * 4/2002 Furr et al. .................. 141/330

* cited by examiner

*Primary Examiner*—Timothy L. Maust
(74) *Attorney, Agent, or Firm*—Cohen, Pontani, Lieberman & Pavane

(57) ABSTRACT

A kit for facilitating filling a hypodermic syringe from a medication vial and disposing of contaminated syringes includes a syringe-filling guide and a sharps holder. The guide has a base for retaining the syringe against relative movement as the syringe plunger is displaced. An attached cover is pivotally closed over the base and, as a vial is inserted into a channel in the base, the syringe needle pierces the vial stopper for drawing the medication therefrom. The cover includes a magnifying lens through which dosage indicia on the syringe are visible in enlarged condition to facilitate filling the syringe. The holder includes a base having a storage chamber, and a cover. A tray of the holder base closes the chamber and has an elongated slot and a plurality of resilient fingers adjacent the slot for supporting a contaminated syringe. As the holder cover closes over the tray, a pusher forces the syringe through the slot into the chamber.

18 Claims, 4 Drawing Sheets

KIT FOR LOADING AND DISPOSAL OF HYPODERMIC SYRINGES USED FOR ADMINISTERING MEDICATION

BACKGROUND OF THE INVENTION

1. Field of the Invention

This invention relates to the field of kits for handling hypodermic syringes used to self-administer medication, and, more specifically, to a kit for assisting patients in drawing medication into hypodermic syringes for self-administering the medication and then disposing of the syringes after use.

2. Description of the Related Art

Many physicians prescribe medications which patients must self-administer through the use of hypodermic syringes, i.e. the patient must inject himself or herself with the medication in the home or otherwise outside of the presence of a health professional such as a doctor or nurse. For example, patients undergoing fertility regimens must be injected by their partners, or diabetics must take insulin, all without going to their doctor's office. The elderly make up a particularly large percentage of those who must undergo such self-administering regimens.

Self-administration makes one step in the dispensing of medication easier, in that the patient does not have to make a trip to the doctor for the medication, but introduces other concerns which must be addressed for the safe and efficacious administration of the medication, as well as the disposal of the contaminated syringe after use.

The physical process of drawing medication into a syringe, and then injecting it into one's own body presents many possible dangers and pitfalls.

First, many patients are understandably nervous or uncertain handling the sharp needle of a hypodermic syringe. A patient having unsteady hands or poor vision is at particular risk of accidental needlesticks, and the knowledge of this risk often increases the uneasiness of the user in his or her handling of the syringe.

Second, having unskilled patients dispense their own medication presents the problem of metering the proper dosage of the medication to be dispensed. The indicia present on the side of most syringes to demark dosages are quite small, and may be difficult to read for some if not most or all patients.

Third, many users may find it difficult to handle the syringe itself during the initial drawing of medication into the syringe from the storage vial, since the process may require some degree of dexterity to complete. The user must hold the vial of medication steady while inserting a sharp hypodermic needle through a hard rubber stopper at an angle near perpendicular. Then, after piercing the stopper with the needle, the combination of the syringe and the vial must be held together with a single hand, while the plunger of the syringe is drawn back with the other hand, to draw the proper amount of medication into the syringe.

It requires no small degree of dexterity to hold the various pieces together, and some manual strength to cause the needle to pierce the stopper.

Furthermore, proper handling of the hypodermic syringe after use is also problematic and hazardous. While the possibility of infection is not present in self-administration, accidental needlesticks after use can themselves be dangerous and must still be avoided.

Finally, once the syringe has been used successfully, it must be disposed of safely, without endangering third parties with possible exposure to the contaminated needle while guarding against accidental needlesticks.

All in all, therefore, the self-administration of medications is fraught with many possible dangers and difficulties, which are not satisfactorily addressed in the prior art.

There is accordingly a need in the art for solutions to these concerns that will render the self-administration of medication through the use of hypodermic syringes safe and effective, without the need for close monitoring by a health professional.

SUMMARY OF THE INVENTION

It is therefore an object of the invention to provide a kit for safely handling of hypodermic syringes used in the self-administration of the medication.

It is a further object of the invention to provide a covered guide for handling of hypodermic syringes for the self-administration of medication, in which the tip of the needle of the syringe is covered by the guide, so that the user thereof is not at risk for accidental needlesticks when inserting the needle into a vial of medication for dispensing of the medication.

It is yet another object of the invention to assist users in properly metering dosages of self-administered medications to be dispensed with hypodermic syringes.

It is a still further object of the invention to provide a safe and effective means for disposing of contaminated hypodermic needles after usage, without exposing third parties to the possibility of accidental needlesticks.

Briefly stated, there is provided a two-component kit for assisting in the handling of contaminated hypodermic needles during and after use. The first component provides a guide for assisting a user in drawing medication from a storage vial into a hypodermic syringe. The vial containing the medication has a conventional self-sealing stopper. The hypodermic syringe has a needle at one end thereof and a plunger disposed therein. The guide includes means for retaining the hypodermic syringe in a first location, in which the needle is exposed, and means for guiding the vial into a second location in which the needle pierces the stopper, thereby permitting the needle to contact the medication. The retaining means retains the hypodermic needle in the first location when the plunger is moved, thereby drawing the medication into the hypodermic syringe for administration by the user. The second component of the kit provides a sharps container or holder for storing the contaminated hypodermic syringes after use, which holder includes a chamber for non-releasably securing and storing the contaminated hypodermic syringes and a resilient support for temporarily supporting holding one of the contaminated hypodermic syringes above the chamber. The holder also includes a pusher member mounted on a movable cover for urging the pusher into contact with a contaminated hypodermic syringes that is supported by the deflectable support. In this fashion, the pusher is movable into contact with and urges downward the contaminated hypodermic syringe, thereby deflecting the resilient support and causing the contaminated hypodermic syringe to non-removeably enter the chamber for its safe retention and disposal.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, in which like reference numerals are applied to like elements.

DETAILED DESCRIPTION OF THE PRESENTLY PREFERRED EMBODIMENTS

The present invention is directed to a kit for assisting users in the self-administration of medication by means of a hypodermic syringe. The kit comprises two components or elements: a guide (illustrated in FIGS. 1–3) for assisting the user in drawing medication from a storage vial into the hypodermic syringe, and a sharps container or holder (illustrated in FIG. 4) for assisting the user in disposing of contaminated hypodermic syringes after their use.

Figure 1:
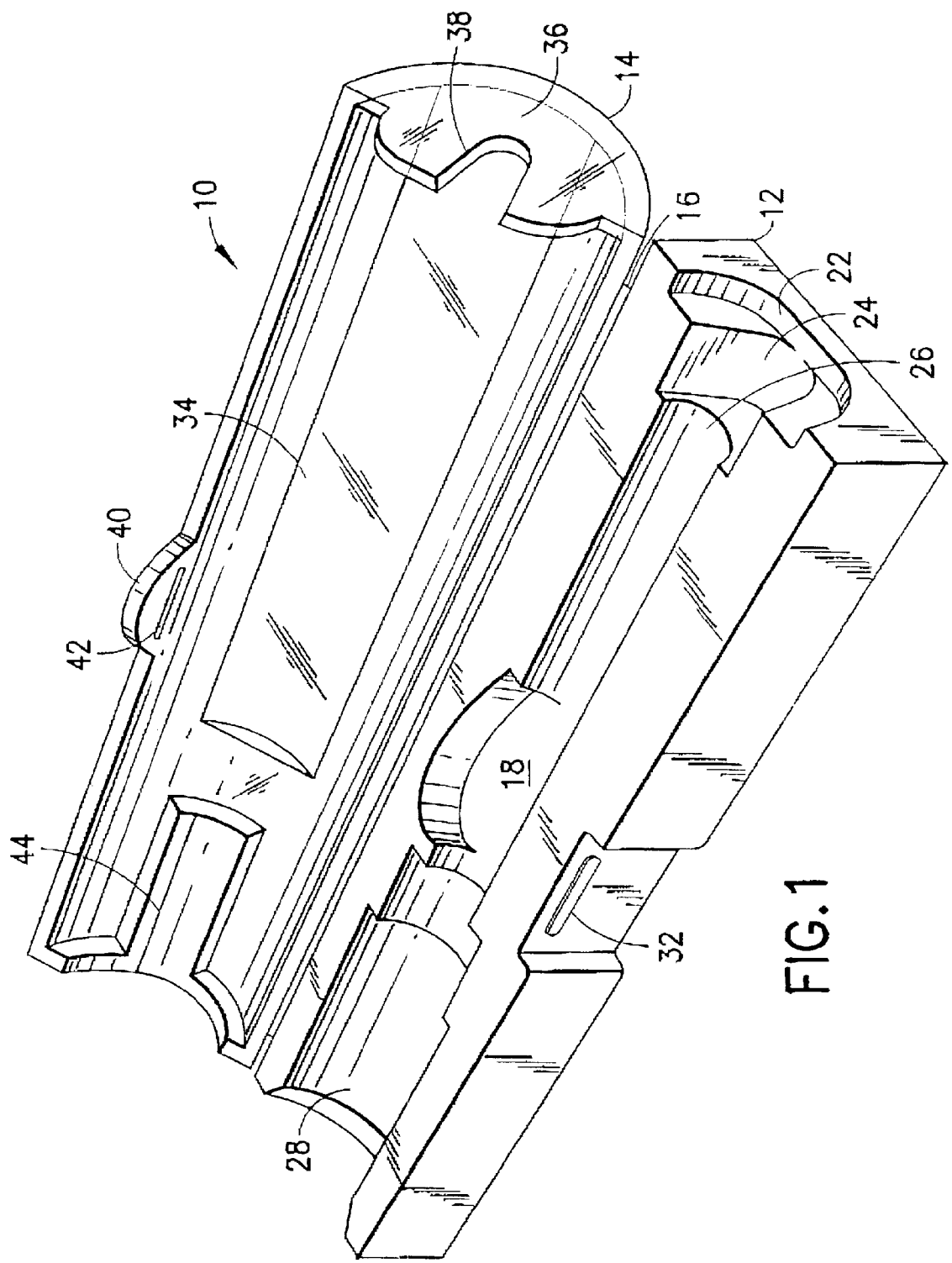
FIG. 1 is a perspective view of the guide component of the invention, shown empty and open.

FIG. 1 depicts a guide 10 constructed in accordance with a preferred embodiment of the invention. Guide 10 includes a base 12 and a hinged cover 14 mounted to base 12 at pivot points 16.

Figure 2:
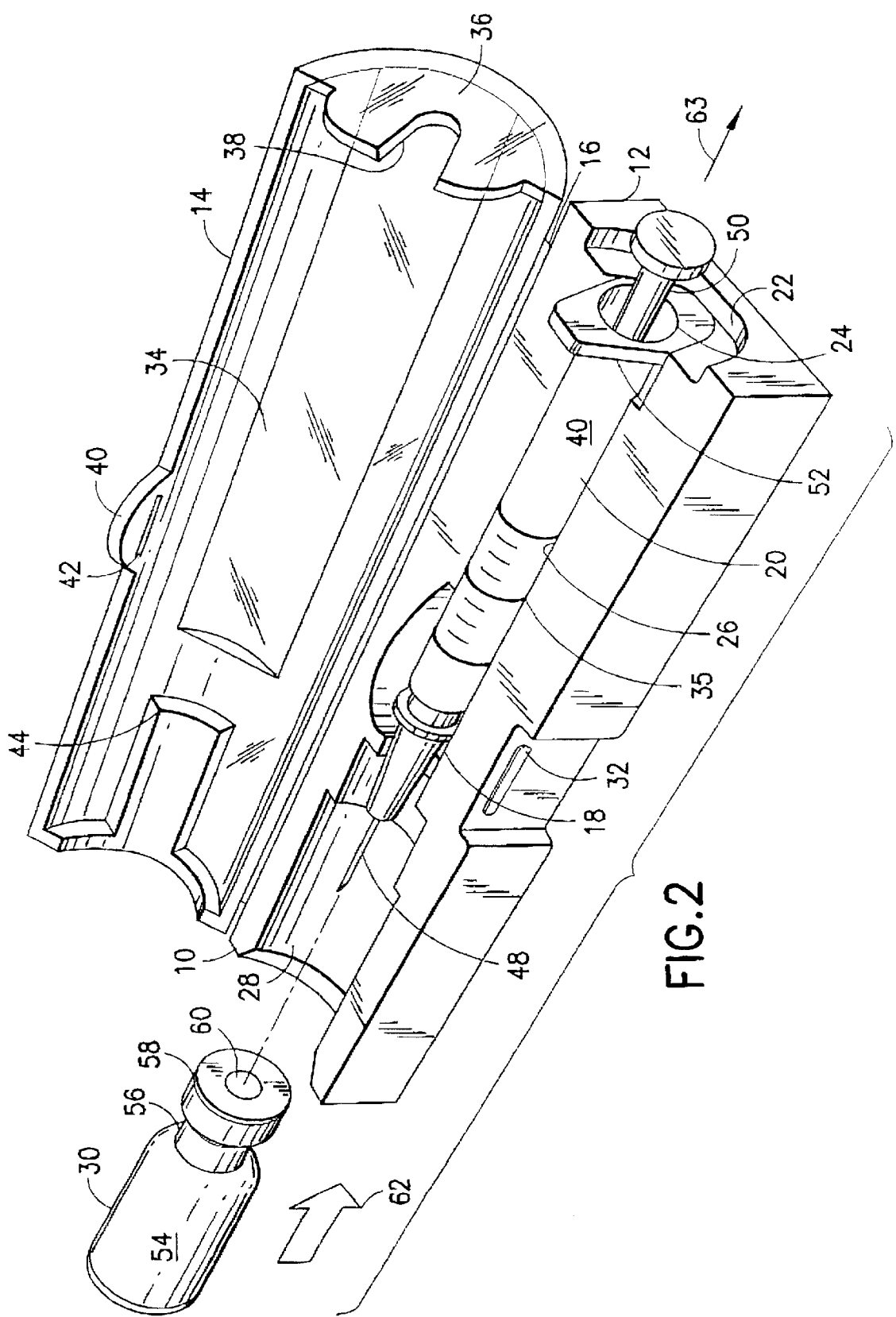
FIG. 2 is a perspective view of the guide component of FIG. 1, shown open with a hypodermic syringe disposed therein and a vial, containing medication, about to be inserted into the guide.
Figure 3:
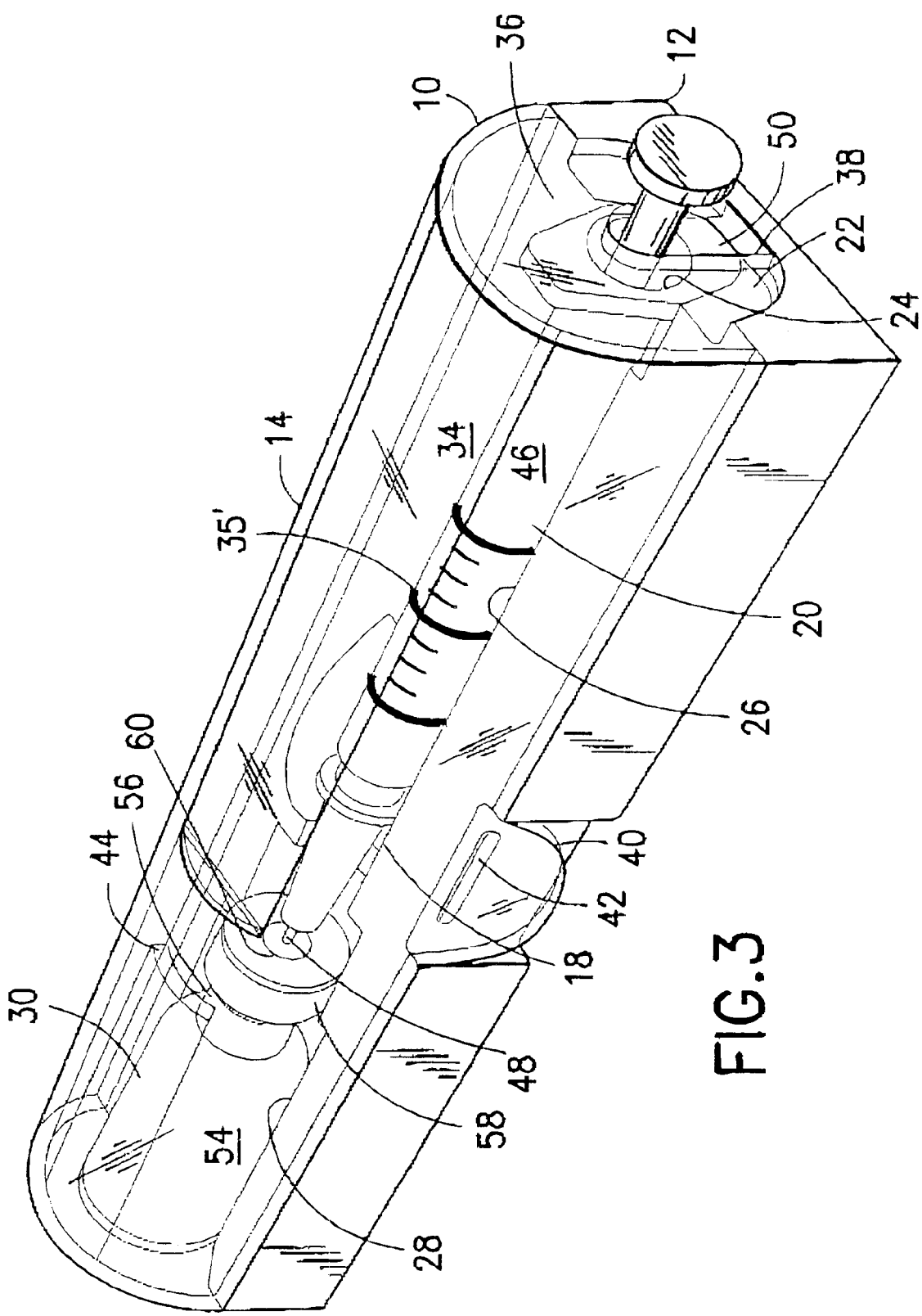
FIG. 3 is a perspective view of the guide component of FIGS. 1 and 2, shown closed, and in which the vial has been inserted so as to enable the drawing of medication from the vial by the hypodermic syringe.
Figure 4:
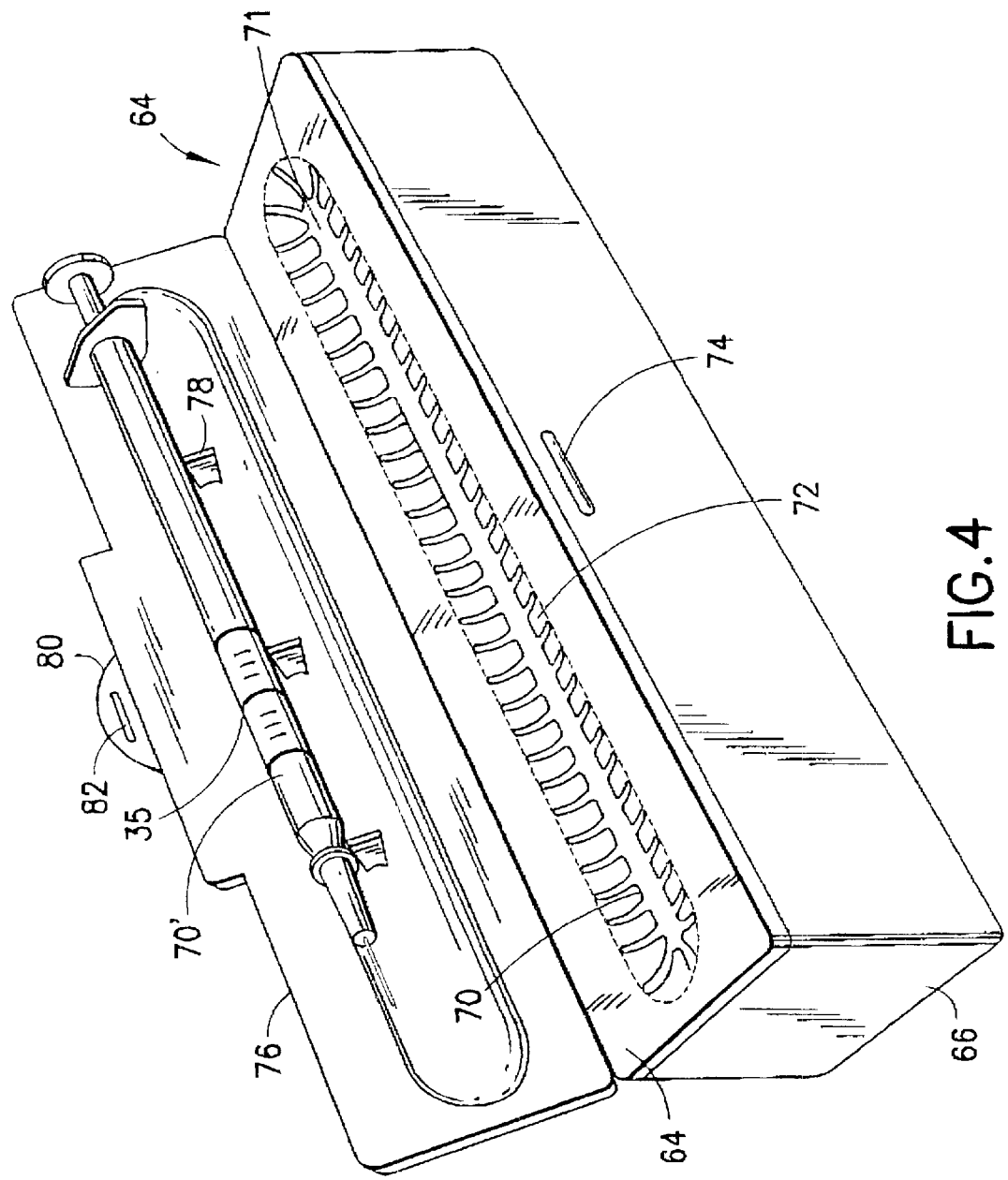
FIG. 4 is perspective view of the inventive sharps container component for holding contaminated hypodermic syringes after use.

Base 12 includes a first well 18 preferably configured to receive a hypodermic syringe 20 (shown in FIGS. 2 and 3). Toward that end, well 18 includes a slot 22 defined near one end of base 12, a recess 24 adjacent slot 22, and a generally semi-cylindrical portion 26 extending inwardly from recess 24 towards the opposite end of base 12.

Base 12 further includes a second well 28, preferably configured to receive a storage vial 30 (FIGS. 2 and 3) that contains a medication in liquid form to be administered to a patient, and a first half of a closure engagement medication, such as by way of example a ridge 32.

Conventionally, vial 30 and hypodermic syringe 20 are both generally cylindrical. First well 18 and second well 28 are therefore configured so that hypodermic syringe 20 and vial 30 are co-axia when disposed therein and, in any event, so that the syringe needle will enter the vial when both are placed in the guide 10 as hereinafter disclosed.

Guide cover 14 is preferably formed of a transparent material, preferably of a suitable a plastic, and includes a magnifying portion 34 so that indicia 35 on hypodermic syringe 20 may be viewed and read more easily through the magnifying portion 34 when the cover 14 is closed over the syringe. Cover 14 further includes a flange 36 having a cutout 38, and a second half of a closure, engaging mechanism such as slotted tab 40, for engagement with the ridge 32. When cover 14 is closed, flange 36 mates with slot 22 of base 12, thereby providing a closure of that end of guide 10, and ridge 32 mates with a slot 42 defined in slotted tab 40, to thereby secure together cover 14 atop base 12.

It will be appreciated by those of ordinary skill in the art that other types of engagement closures may alternatively be provided to secure cover 14 and base 12 together, such, for example, as clips, snaps, tongue and groove closures, etc., and that the choice of closure is a mere matter of design choice for the rountineer.

Cover 14 also preferably includes an alignment block 44 for correspondingly positioning, holding and aligning vial 30 when it is placed in guide 10.

The operation of guide 10 may be best understood best by reference to FIGS. 2 and 3 and the following description of the configuration of the conventional hypodermic syringe 20 and vial 30 depicted therein.

Hypodermic syringe 20 includes a cylindrical barrel 46 with a hollow hypodermic needle 48 extending from one end thereof. Hypodermic needle 48 provides an internal conduit for communication between the exterior of syringe 20 and the interior thereof, in known fashion. As is also known, hypodermic needle 48 is conventionally disposed co-axially with cylindrical barrel 46. A plunger 50 is located at the opposite end of cylindrical barrel 46. Plunger 50 fits into the interior of cylindrical barrel 46 and may be initially displaced outwardly in one direction to pull a fluid into cylindrical barrel 46 and then displaced inwardly in the opposite direction to dispense fluid therefrom.

To assist in the use of and the administration of medication from hypodermic syringe 20, cylindrical barrel 46 also conventionally includes a finger grip 52, so that the user may have a surface against which to push when depressing plunger 50 to dispense medication from hypodermic syringe 20.

Vial 30 includes a generally cylindrical housing 54 topped by a narrowed neck 56. A stopper 58 having a piercable self-sealing portion 60 closes neck 56. Self-sealing portion 60 is generally aligned and centered with neck 56.

The use of guide 10 commences with the insertion of hypodermic syringe 20 into guide 10. To do so with the guide cover 14 open, the user inserts a clean, unused hypodermic syringe into the tray of base 12 by aligning cylindrical barrel 46 with semi-cylindrical portion 26 of base 12 and placing finger grip 52 into recess 24. To accommodate varying sizes of syringe recess 24 may optimally be sized slightly larger than the largest syringe finger grip 52 with which it is to be used.

When hypodermic syringe 20 is so positioned, hypodermic needle 44 extends over second well 28. Cover 14 is then moved into its closed position (FIG. 3) by pivoting cover 14 about pivot points 16 until ridge 32 mates with slot 42, thereby establishing an engagement closure between cover 14 and base 12. Plunger 50 extends through cutout 38 in flange 36, giving the user access thereto.

A medication-containing storage vial 30 is then slideably advanced in the direction shown by arrow 62 (FIG. 2) into second well 28 until and beyond the point at which hypodermic needle 48 pierces self-sealing stopper 60, thereby allowing the user to withdraw the medication contained in vial 30. be advancement of the vial is completed when a portion of the vial abuts an appropriate surface boundary or adjacent second wall 20.

Medication is withdrawn from vial 30 through hypodermic needle 48 into the interior of cylindrical barrel portion 46 by the user's selective pulling back of plunger 50 in the direction of arrow 63 (FIG. 2). Hypodermic syringe 20 is restrained from lateral movement in the direction of travel of plunger 50 since finger grip 46 will abut flange 36. This enables the user to conveniently withdraw the medication from vial 30 without exposing himself or herself to the sharp point of hypodermic needle 42 and without having to hold vial 30 and hypodermic syringe 20 together with one hand while pulling back on plunger 50, with the other as heretofore required.

In addition, with cover 14 in its closed position, magnifier 34 enlarges any indicia present on hypodermic syringe 20, thereby making it easier to meter the dosage of medication drawn into hypodermic syringe 30. Thus, as the user pulls back on plunger 50 to draw medication from the vial into the syringe, the user can view the indicia 35' on the syringe body, through the magnifying lens 34, to better and more accurately determine the amount of liquid contained in the syringe for injection in accordance with the orders of the prescribing health professional.

Use of guide 10 accordingly permits the simple, safe, effective and dosage-accurate drawing of medication from a vial 30, into a syringe 20 for injected administration of the medication to a patient.

Once the medication has been injectingly administered, the user must safely dispose of the contaminated hypodermic syringe 20.

For this purpose, inventive sharps container or holder 64 (FIG. 4) is provided.

Holder 64 includes a chamber 66 sized to receive at lease one, and preferably a plurality, of contaminated hypodermic syringes. The length and width of the chamber should be larger than the largest hypodermic syringe with which chamber 66 is to be used, and its depth should be selected to accommodate the number of contaminated hypodermic syringes with which holder 64 is intended for use in a single application or administration regimens.

Chamber 66 is defined a five-sided open box, with its sixth side covered by a preferably non-removable tray-like panel 68 having a recessed well 70 therein. Recessed well 70 is sized to accommodate the particular contaminated hypodermic syringes with which holder 64 is to be used. The bottom of recessed well 70 is comprised of an elongated slot 71 and a plurality of resiliently deformable fingers 72 located adjacent transured to and along the slot. A first half of an engagement closure, such, for example, as a ridge 74, is formed on the exterior of the box that defines chamber 66.

Holder 64 further comprises a cover 76, pivotably hinged to the box of chamber 66, having at least one (and preferably a plurality of) projection(s) 78 depending therefrom. Projections 78 are sized to extend to or below the bottom of recessed well 70 when cover 76 is in its closed position atop chamber 66.

Cover 78 also carries a second half of an engagement closure, such as a slotted tab 80, for mating engagement with the first half of the closure, as for example by way of a slot 82 in slotted tab 80 for mating engagement with ridge 74.

Holder 64 provides for the safe and efficient non-releasable receipt and storage of contaminated hypodermic syringes after their use.

In use, and with the cover 78 of holder 64 open, the user places a contaminated hypodermic syringe 20' onto the tray overlying chamber 66 so that the syringe is supported in recessed well 70. More particularly, resilient fingers 72 supportably hold contaminated hypodermic syringe 20' above chamber 66. The user then pivotally closes cover 76, causing projections 78 to contact contaminated hypodermic syringe 20' and urge the syringe downward. This action deflects resilient fingers 72, momentarily widening slot 71 and thereby opening a one-way passageway into chamber 66, to deposit contaminated hypodermic syringe 20' in chamber 66 where it is maintained out of contact with any person until it is subsequently discarded. The closure of cover 76 also causes engaging closure to be effected between ridge 74 and slot 82. As was the case with the closure provided by ridge 32 and slot 42 of guide 10, any convenient alternate manner of or component or effecting retained closure of holder 64 may be selected as a matter of design choice by the rountineer.

In a preferred embodiment, of holder 64, three projections 78 may be provided, and optionally spaced so that they are located for syringe-dispensing movement into the spaces between adjacent resilient fingers 72 of recessed well 70 when the cover is closed, thereby avoiding exertion of unnecessary pressure on resilient fingers 72, which could potentially deform them against reuses.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A kit for assisting a user in drawing a liquid medication from a storage vial having a pierceable self-sealing stopper into a hypodermic syringe having a needle, a displaceable plunger and dosage indicia imprinted on the syringe, and for safe disposal of the syringe after use, said kit comprising:

a guide for assisting the user in drawing medication from the vial into the hypodermic syringe, said guide comprising:
a guide base configured for receiving the syringe in a first location of the base so that the needle of the syringe projects into a second location of the base and for releasably retaining the syringe in said first location against movement of the syringe relative to the base while permitting user-controlled displacement of the plunger of the retained syringe relative to the base, and a guide cover engageable with said base to nonreleasably enclose and retain the syringe in the first location of the base with the guide cover in closed condition on said base, said guide base being further configured for guiding the vial into a releasably retained inserted position in said second location of the base so that, as the vial is guided into said second location with the syringe in said first location, the syringe needle pierces into and through the vial stopper into contact with the liquid medication in the vial and so that, as the plunger of the base-retained syringe is selectively outwardly displaced under user control to fill the syringe with medication from the vial in said inserted position of the vial, the medication in the vial is drawn into the syringe through the syringe needle, and said guide cover further including a magnifying lens integrally located on said cover so that, when the syringe is positioned in said first location of the base and the cover is in said closed condition, the dosage indicia on the syringe are viewable by a user through the cover magnifying lens in a visually-enlarged state to thereby facilitate user filling of the syringe with medication from the vial in a user-controllable desired amount in accordance with a predetermined dosage to be administered to the user by way of the syringe; and a holder for nonreleasably and captively storing a contaminated hypodermic syringe after use of the syringe, said holder comprising:

a holder base defining a chamber for nonreleasably receiving and retaining a contaminated hypodermic syringe, a tray on said base and closing said chamber, said tray comprising an elongated slot defined in said tray and a resilient support proximate said slot for supportably holding a contaminated hypodermic syringe placed by a user on said resilient support above said chamber, and a holder cover engageable with said holder base for closing the holder cover about said tray, said holder cover carrying a pusher member projecting inwardly from the cover and located and configured so that, as the holder cover is closed about the tray, said pusher member contacts and displaces a contaminated syringe supported on the tray into resiliently-deforming contact with the resilient support and through the elongated slot to thereby force the contaminated syringe into said chamber for nonreleasably captured storage of the contaminated syringe in said chamber.

2. The kit of claim 1, wherein said guide base further includes a stop for preventing backward movement of said syringe when said plunger is displaced.

3. The guide of claim 2, wherein said stop includes a recess configured to permit said plunger to move freely along an axis of said syringe, while said syringe is retained in said first location.

4. The kit of claim 1, wherein said guide cover further includes means for covering said needle when said vial is guided into said second location.

5. The kit of claim 1, wherein said guide cover is transparent.

6. The kit of claim 1, wherein said guide cover is pivotably mounted to said guide base.

7. The kit of claim 1, wherein said guide base further includes means for centering said vial along an axis of said needle of said syringe.

8. The kit of claim 1, wherein said resilient support includes a plurality of resilient fingers.

9. The kit of claim 1, wherein said holder cover is pivotably mounted to said holder base.

10. A guide for assisting a user in drawing medication from a vial into a hypodermic syringe, said guide comprising:

a guide base configured for receiving the syringe in a first location of the base so that the needle of the syringe projects into a second location of the base and for releasably retaining the syringe in said first location against movement of the syringe relative to the base while permitting user-controlled displacement of the plunger of the retained syringe relative to the base, and a guide cover pivotably mounted to said base to nonreleasably enclose and retain the syringe in the first location of the base with the guide cover in closed condition on said base, said guide base being further configured for guiding the vial into releasably retained inserted position in said second location of the base so that, as the vial is guided into said second location with the syringe in said first location, the syringe needle pierces into and through the vial stopper into contact with the liquid medication in the vial and so that, as the plunger of the base-retained syringe is selectively outwardly displaced under user control to fill the syringe with medication from the vial in said inserted position of the vial, the medication in the vial is drawn into the syringe through the syringe needle, and said guide cover further including a magnifying lens integrally located on said cover so that, when the syringe is positioned in said first location of the base and the cover is in said closed condition, the dosage indicia on the syringe are viewable by a user through the cover magnifying lens in a visually-enlarged state to thereby facilitate user filling of the syringe with medication from the vial in a user-controllable desired amount in accordance with a predetermined dosage to be administered to the user by way of the syringe.

11. The guide of claim 10, wherein said guide base further comprises a stop for preventing backward movement of said syringe when said plunger is displaced.

12. The guide of claim 11, wherein said stop includes a recess configured to permit said plunger to move freely along an axis of said syringe, while said syringe is retained in said first location.

13. The guide of claim 10, wherein said guide cover further includes means for covering said needle when said vial is guided into said second location.

14. The guide of claim 10, wherein said guide cover is transparent.

15. The guide of claim 10, wherein said guide base further includes means for centering said vial along an axis of said needle of said syringe.

16. A holder for nonreleasably and captively storing a contaminated hypodermic syringe after use of the syringe, said holder comprising:

a holder base defining a chamber for nonreleasably receiving and retaining a contaminated hypodermic syringe, a tray on said base and closing said chamber, said tray comprising an elongated slot defined in said tray and a resilient support proximate said slot for supportedly holding a contaminated hypodermic syringe placed by a user on said resilient support above said chamber, and a holder cover engageable with said holder base for closing the holder cover about said tray, said holder cover carrying a pusher member projecting inwardly from the cover and located and configured so that, as the holder cover is closed about the tray, said pusher member contacts and displaces a contaminated syringe supported on the tray into resiliently-deforming contact with the resilient support and through the elongated slot to thereby force the contaminated syringe into said chamber for nonreleasably captured storage of the contaminated syringe in said chamber.

17. The holder of claim 16, wherein said resilient support includes a plurality of resilient fingers.

18. The holder of claim 16, wherein said holder cover is pivotably mounted to said holder base.

* * * * *